United States Patent [19]

Glover

[11] 4,075,883
[45] Feb. 28, 1978

[54] ULTRASONIC FAN BEAM SCANNER FOR COMPUTERIZED TIME-OF-FLIGHT TOMOGRAPHY

[75] Inventor: Gary H. Glover, Schenectady, N.Y.

[73] Assignee: General Electric Company, Schenectady, N.Y.

[21] Appl. No.: 716,109

[22] Filed: Aug. 20, 1976

[51] Int. Cl.² .......................................... G01N 29/00
[52] U.S. Cl. ..................................... 73/620; 73/628; 128/2 V
[58] Field of Search .................. 73/67.5 R, 67.7, 67.6, 73/67.8 R, 67.8 S, 67.9; 340/1 R, 3 R, 5 MP, 9; 128/2 V, 2.05 Z

[56] References Cited

U.S. PATENT DOCUMENTS

| 3,794,964 | 2/1974 | Katakura | 340/1 R |
|---|---|---|---|
| 3,940,625 | 2/1976 | Hounsfield | 250/360 |
| 3,959,770 | 5/1976 | Schaefer | 340/5 MP |

OTHER PUBLICATIONS

Greenleaf et al, "Algebraic Reconstruction of Spatial Distributions of Acoustic Velocities in Tissue," Acoustical Holography, vol. 6, 1975, pp. 71-90.
Knollman et al, "Real Time Ultrasonic Imaging Methodology in Nondestructive Testing," Journal of Acoustical Society of Amer., vol. 58, No. 2, pp. 455-470, Aug. 1975.
Von Ramm et al, "Cardiovascular Diagnosis with Real Time Ultrasound Imaging," Acoustical Holography, vol. 6, 1975, pp. 91-95.

Primary Examiner—Richard C. Queisser
Assistant Examiner—Stephen A. Kreitman
Attorney, Agent, or Firm—Donald R. Campbell; Joseph T. Cohen; Jerome C. Squillaro

[57] ABSTRACT

A fast ultrasonic scanner for soft tissue imaging and/or characterization has a transmitter with a divergent beam pattern and an arcuate array of receivers. The propagation delay time of a short acoustic pulse traversing a water bath and immersed specimen depends on the velocity distribution and is detected at each receiver. Digital data is derived from the receiver signals at many angular positions of the scan apparatus and is used to compute a reconstruction of the velocity distribution in the specimen. The instrument provides quantitative measurements of bulk tissue and has application in breast examination and mass screening for breast cancer.

11 Claims, 13 Drawing Figures

ULTRASONIC FAN BEAM SCANNER FOR COMPUTERIZED TIME-OF-FLIGHT TOMOGRAPHY

BACKGROUND OF THE INVENTION

This invention relates to acoustic apparatus for use in the imaging or characterization of biological tissue and, more particularly, to an ultrasonic fan beam scanner for time-of-flight computerized tomography which is especially useful in breast and other soft tissue examination.

Computerized x-ray tomographic systems are at present well known and provide to medical practitioners high accuracy measurements of x-ray absorption coefficients in soft tissue. These scanners utilize ionizing radiation, however, and may be potentially destructive to the imaged tissue when used for human examination. General information on these techniques is given in a magazine article entitled "Image Reconstruction from Projections" in Scientific American, Oct. 1975, Vol. 233, No. 4, pp. 56–68.

Ultrasonic imaging systems are noninvasive and are nondestructive so far as is presently known. The most widely used technique is the pulse echo B-scan mode, or variants thereof, in which a video display employs intensity modulation to depict echo return amplitude as a function of depth. The echoes are generated at interfaces between media of different acoustic impedance within the specimen tissue. However, the magnitude of the interfacial reflection coefficient depends not only on the impedance ratio, but also on the angle of incidence of the beam, and furthermore the echo amplitude is reduced due to attenuation from the intervening tissue. Thus, the images generated by B-scan systems describe geometry and topology of interfaces, which can be interpreted qualitatively but do not give quantitative information on bulk tissue due to geometric distortion of the echo amplitude arising from refraction, specular reflection, and diffraction. Similarly, ultrasound transmission systems based on amplitude suffer from the same limitations. As applied to human breast imaging by echography, it has been observed that characteristic echo patterns accompany various types of breast leasions, and clinical diagnosis is thus effected mainly by a subjective pattern recognition process.

The problems associated with absorption or reflection amplitude are eliminated by a system based on propagation velocity of the ultrasonic wave, which is easily measured by detecting the time of passage of an ultrasound pulse transmitted through the specimen over a known path length. The concept of computerized time-of-flight (TOF) tomography for reconstruction of two-dimensional velocity distributions using a pencil beam geometry is discussed in the article by J. F. Greenleaf et al, entitled "Albebraic Reconstruction of Spatial Distributions of Acoustic Velocities in Tissue From Their Time of Flight Profiles," Acoustical Holography, Plenum Press, Vol. 6, pp. 71–89 (1975). This apparatus employed diametrically opposing transducers which were rectilinearly scanned while rotating the transducers incrementally between scans. Such an instrument is not clinically acceptable, however, because of the relatively long scan times and attendant poor image quality caused by patient motion during the scan.

SUMMARY OF THE INVENTION

An ultrasonic scanner for improved rapid-scan breast and other soft tissue examination employs a rotatable scan apparatus with a transmitter transducer assembly for producing an ultrasound fan beam pattern and an arcuate receiver transducer array for detecting the arrival of a short acoustic pulse propagating along many divergent paths through a liquid path and tissue specimen to each receiver. The time of arrival at the receiver is a function of the velocity distribution along the particular path. This information upon being supplied to a computer can be utilized to obtain a reconstruction of the velocity distribution in the specimen and displayed either as a visual image or in numeric format. This is a quantitative measurement of the bulk tissue's acoustic properties and as presently understood has value in medical diagnosis.

The scan apparatus includes a water or liquid tank which in the preferred embodiment is generally sector-shaped with openings in opposing end walls for receiving a single transmitter with a divergent lens and the arcuate receiver array. Means are provided for rotating the scan apparatus and for exciting the transmitter transducer to generate acoustic pulses at selected angular positions of the scan apparatus. Data acquisition circuitry is operative at each angular position to derive projection output data indicative of the propagation delay times of the acoustic pulse upon detection by the individual receiver transducers. The ensemble of projection output data for the respective angular positions form transmission time-of-flight projections to be used in combination to reconstruct velocity distributions at known coordinates in a layer of the specimen. Preferably the data acquisition system has parallel processing channels, one per receiver, each including a pulse height discriminator for generating a delay time stop signal. The stop signal and a start electrical pulse produced by a pulser for initiating generation of an acoustic pulse, or a delayed start pulse, are used in either integrating or in digital timing type circuits to derive digital projection output data. In another embodiment requiring multiple acoustic pulses at each scan apparatus angular position, rather than one acoustic pulse, a small number of data acquisition channels are time shared by sets of receiver transducers to reduce equipment requirements. Instead of using a single comparator functioning as a receiver signal pulse height discriminator, positive and negative comparators in parallel, with further capability to generate a correction bit, result in more accurate time-of-flight measurements.

The scanner further includes a memory unit for storing projection output data, and typically has provision for translation of the scan apparatus along its rotational axis to derive projection output data at several axial positions to be used to reconstruct velocity distributions for a plurality of parallel specimen layers. Stored projection output data can be fed to the computer, which forms no part of this invention, or read into a magnetic tape recorder and later taken to a central computer for processing. In view of the rapid scan feature, the noninvasive nature of ultrasound, and indications that neoplastic lesions embedded in normal tissue can be quantitatively identified, an application of the ultrasonic fan beam scanner is mass screening for breast cancer.

DESCRIPTION OF THE PREFERRED EMBODIMENTS

Figure 1:
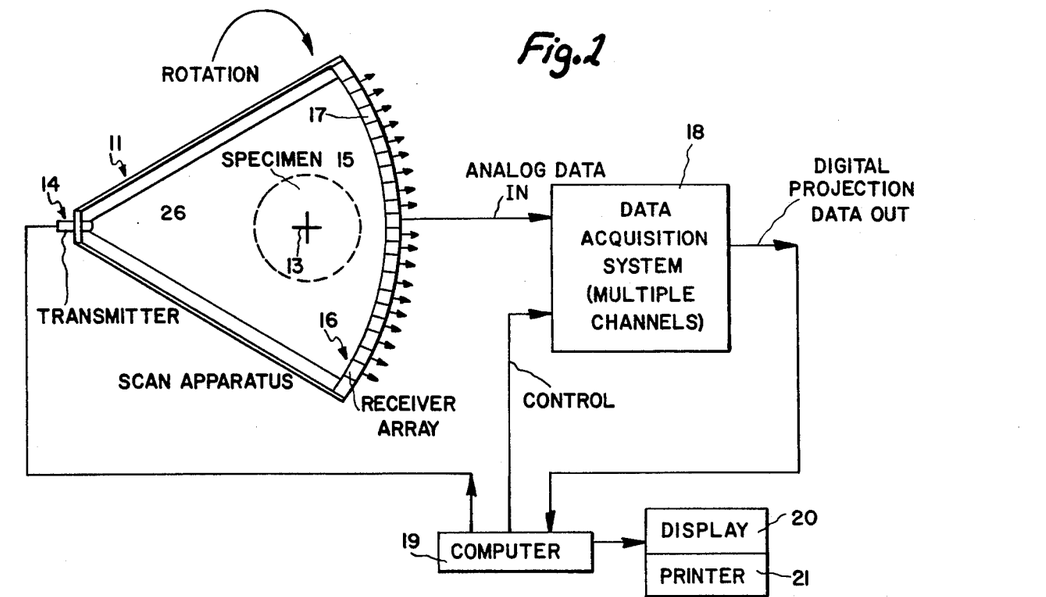
FIG. 1 is a simplified diagram of the time-of-flight ultrasound computerized tomography system with a rotatable fan beam scan apparatus and data acquisition circuitry as herein taught.

The basic components of a rapid scan ultrasonic time-of-flight computerized tomography system especially useful for soft biological tissue imaging and/or characterization are depicted in simplified diagrammatic form in FIG. 1. The technique to be described is based on computerized reconstruction of two-dimensional velocity distributions from one-dimensional time-of-flight projections. The preferred embodiment is explained with regard to an ultrasonic fan beam scanner for human breast examination, but various other applications are within the scope of the invention as more broadly defined. A significant feature of this ultrasound instrument is the use of divergent beam geometry to enable fast scan data collection for examining live tissue specimens in a time short enough to eliminate patient motion artifacts. Another significant feature is the ability to provide highly quantitative measurements of the acoustic properties of the bulk specimen.

Figure 2:
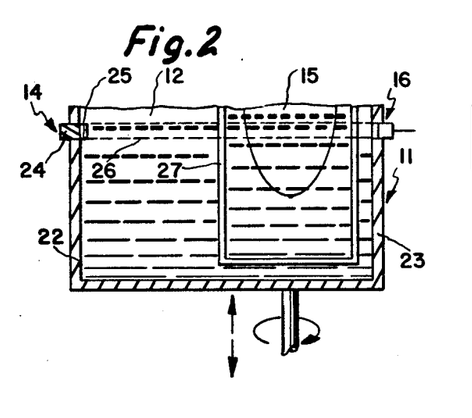
FIG. 2 is a schematic longitudinal cross-sectional view through the ultrasound scan apparatus shown in top view in FIG. 1.

Referring also to FIG. 2, the ultrasonic fan beam scan apparatus includes a tank 11 that is filled with water or other suitable liquid 12 and has a vertical rotational axis 13. Liquid tank 11 carries a transmitter transducer assembly 14 capable of producing a fan-shaped ultrasound pattern which propagates through the water bath and tissue specimen 15 immersed therein, and is detected by an arcuate receiver transducer array 16 comprised by a plurality of individual receiver elements 17 arranged in an arc. Thus, short acoustic pulses generated by transmitter assembly 14 travel along many diverging paths, and a particular acoustic pulses arrives at an individual receiver element 17 at a time dependent on the velocity distribution through which the ray travelled. As will be further explained, the ensemble of measurements of time-of-flight or propagation delay time from all the receiver elements in array 16 forms one transmission time-of-flight projection. Analog data representing propagation delay times of the acoustic pulse upon detection at individual receiver transducers are acquired simultaneously by parallel channels of electronics in a data acquisition system 18, so that the output digital projection data for the entire projection is available for transmission to a digital computer 19. The water tank 11, transmitter transducer assembly 14 and arcuate receiver transducer array 16 rotate about the fixed specimen 15 at the center of reconstruction. The transmitter is triggered at equally spaced angular or azimuth positions of the scan apparatus to obtain time-of-flight projections at many angles relative to a fixed coordinate system in the specimen. At each angular position of the scan apparatus, under control of computer 19, digital projection output data is derived in data acquisition system 18 and fed to the computer. The transmission time-of-flight projections are then utilized in combination to reconstruct velocity distributions using algorithms similar to those in x-ray reconstruction programs The computed reconstruction of velocity distributions is supplied to a visual display device 20 such as a cathode ray tube, and can also be printed out in numeric format using a printer 21. The result is a "tomogram" for a horizontal slice or layer of the specimen. The entire scan apparatus translates vertically along rotational axis 13 to acquire other complete sets of projection output data to be used to reconstruct velocity distributions for additional parallel specimen layers.

Figure 3:
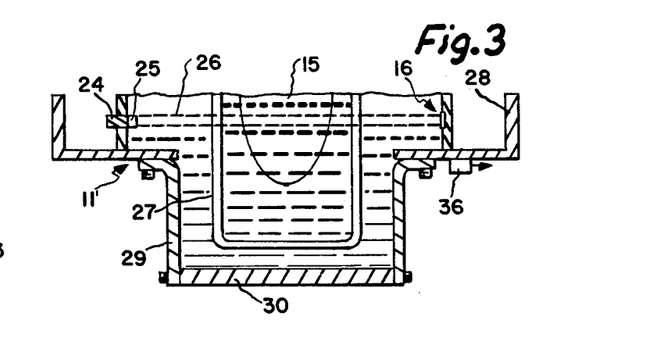
FIG. 3 is a modification of the scan apparatus in FIG. 2.

Other mechanical features of two forms of the rotatable scan apparatus are illustrated in FIGS. 2 and 3. In FIG. 2, liquid tank 11 is generally sector-shaped (see also FIG. 1) with a pair of diverging side walls and opposing end walls 22 and 23 respectively having openings in which are mounted transmitted transducer assembly 14 and arcuate receiver transducer array 16. Transmitter 14 is made up of a single transducer element 24 with an attached divergent lens 25 for producing a planar fan-shaped ultrasonic beam 26. With the patient in a prone position lying face down with one breast immersed in a water bath within an inner container 27, a horizontal slide approximately 5 millimeters thick perpendicular to the breast axis is then imaged. Outer tank or container 11 is relatively deep and is made, for example, of Plexiglas ® (trademark of Rohm & Haas Company). For purposes of illustration, the solid bottom tank wall is attached to a shaft which has both rotational and vertical motion. Liquid tank 11' in FIG. 3 is also generally sector-shaped, but is much shallower with overflow tank members 28 at either end and a circular aperture in the bottom wall somewhat larger in diameter than inner container 27. An outer flexible container 29 is attached to the bottom wall at the edges of this aperture, and while the second flexible container is depicted as having a solid bottom wall member 30, in practice there may be provision for admitting water to and draining water from the inner container and the outer container and tank. For further information on a mammography instrument including a pivotable patient support that can be used in conjunction with the present ultrasonic fan beam scanner, reference may be made to allowed application Ser. No. 600,874, now U.S. Pat No. 3,973,126, by R. W. Redington and J. L. Henkes, Jr., entitled "Mammography," filed on July 31, 1975 and assigned to the assignee of this invention. The disclosure of this patent is incorporated by reference herein.

Figure 4:
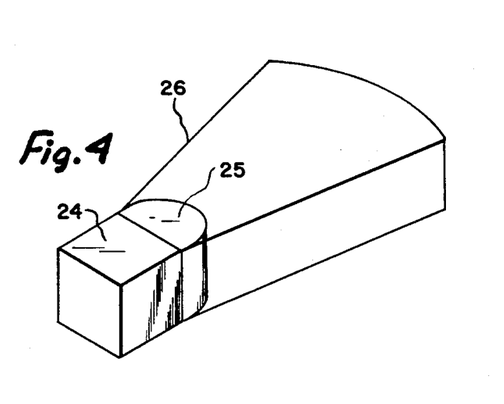
FIG. 4 is a perspective view of the transmitter and divergent lens and the generated planar fan-shaped ultrasounc beam.
Figure 5:
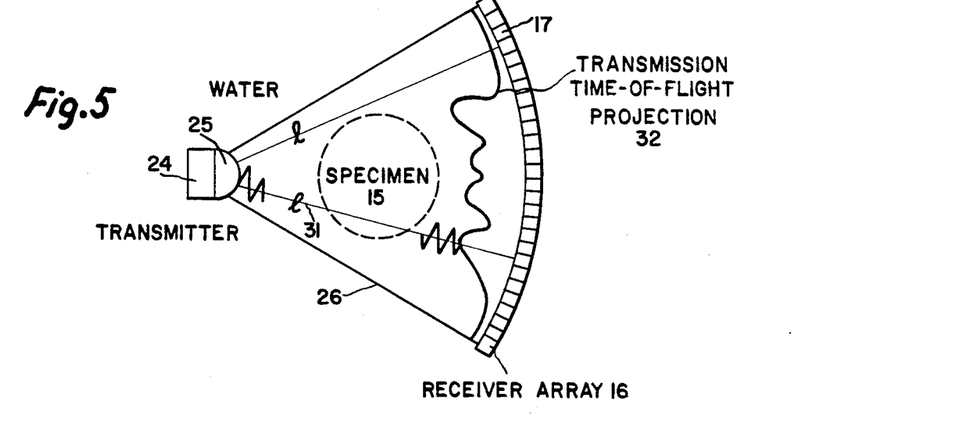
FIG. 5 is a diagrammatic top view of the transmitter and receiver array further illustrating a single acoustic ray and a sample transmission time-of-flight projection representing the ensemble of propagation delay times detected individually at the receivers.

Referring to FIGS. 4 and 5, transmitter 24 and individual receivers 17 are electroacoustic transducers such as piezoelectric elements. This type of transmitter transducer generates a short acoustic pulse upon being shock excited by a narrow rectangular electrical pulse or by the trailing edge of a sawtooth pulse. Divergent lens 25 attached to transmitter transducer 24 is made for example of lucite or Plexiglas ® and has a semicircular cross section so as to produce the relatively narrow, planar ultrasound fan beam 26. For purposes of analysis, the diverging fan beam is considered to be composed of a plurality of acoustic rays 31 of path length $l$, equal in number to the individual receivers 17. In one example of the practice of the invention, there are 128 individual receivers 17 extending over an arc length of about 60°. Assuming that specimen 15 is immersed in a water bath, a short ultrasound pulse launched from transmitter 24 traverses the specimen along path $l$ until arrival at one receiver 17. The time of arrival at the receiver is a function of the velocity distribution along the path and is given by the line integral $$t_\theta = \int_l \frac{ds}{v},$$

where $\theta$ defines the ray path $l(\theta)$, $ds$ is an incremental distance along the path, the $v$ is the velocity. In determining the time of arrival, the first excursion of the acoustic pulse greater than the predetermined noise level is detected. The ensemble of time-of-flight or propagation delay time data for all receivers, upon conversion to digital form, forms a transmission time-of-flight projection 32. In computer calculations of reconstructions of velocity distributions, it is desirable to use a time-of-flight projection which is normalized with respect to the propagation velocity $v_o$ in the waterbath surrounding the specimen. The normalized time-of-flight projection is then a one-dimensional projection of the change in propagation delay time due to insertion of the specimen. This system constant along with other such constants are accounted for in the computer algorithm. The accuracy of reconstruction is unaffected by amplitude losses due to the reflection and refraction of an acoustic ray. However, some aberrations may result from departure of the rays from straight paths due to refraction, although such aberrations can be reduced or accounted for in the computer program.

A large number of transmission time-of-flight projections 32, in the form of digital projection output data, are obtained by successively rotating the scan apparatus to a large number of angular positions, such as 100 positions. These sets of output data are then utilized to reconstruct the velocity distribution in a Cartesian coordinate system centered on the axis of rotation.

Figure 6:
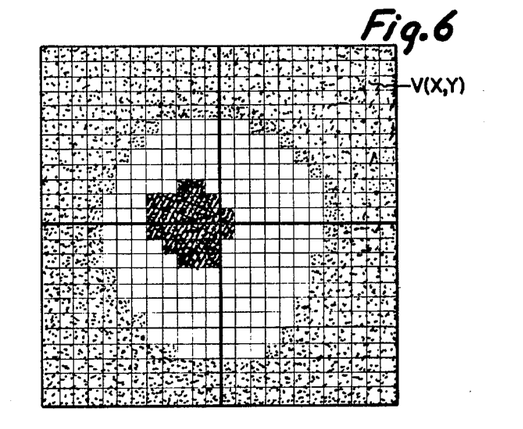
FIG. 6 illustrates a portion of a display device divided into pixels that respectively display reconstructed velocity values to form an image of the specimen slice.

The computed results are formulated as velocity values assigned to picture elements or pixels in a coordinate system encompassing the specimen region (see FIG. 6). A video image may be obtained by gray scale or pseudo-color encoding of the various velocity values $v(x,y)$ on a cathode ray tube display. Alternatively, the velocity values can be printed out in a similar arrangement of rows and columns. For breast examination, the reconstruction velocity in each pixel is represented as a "CTU number" defined by $$CTU = 1000\,(v-v_o)/v_o,$$

where $v$ is the reconstructed velocity and $v_o$ is the velocity in water. Thus $+10$ CTU corresponds to a velocity 1 percent higher than water, whereas $-$CTU members correspond to a velocity lower than water. In the numeric form of display, these are the numbers printed out by the printer. The images are formatted, of course, so that a front view of the breast is portrayed. In summar, the reconstruction is a "tomogram" in which velocity values are digitally determined in a rectilinear array at discrete positions in the specimen. The significance of this concept is that the results are a direct measurement of a bulk tissue acoustic property, in particular velocity, as a function of position. Although it will be understood that larger test samples are needed to confirm preliminary studies, preliminary testing of a small number of samples indicates that velocity gives medically useful information. For example, for an older age group of women which includes the highest risk group for breast cancer, mammory fat has a velocity lower than water whereas tumors have a velocity greater than water. Thus, if a gray scale imaging system is used with black representing the highest velocity and white the lowest velocity, tumors are displayed as black masses. It may also be possible to differentiate different types of tumors on the basis of their velocity numbers.

Figures 7, 8:
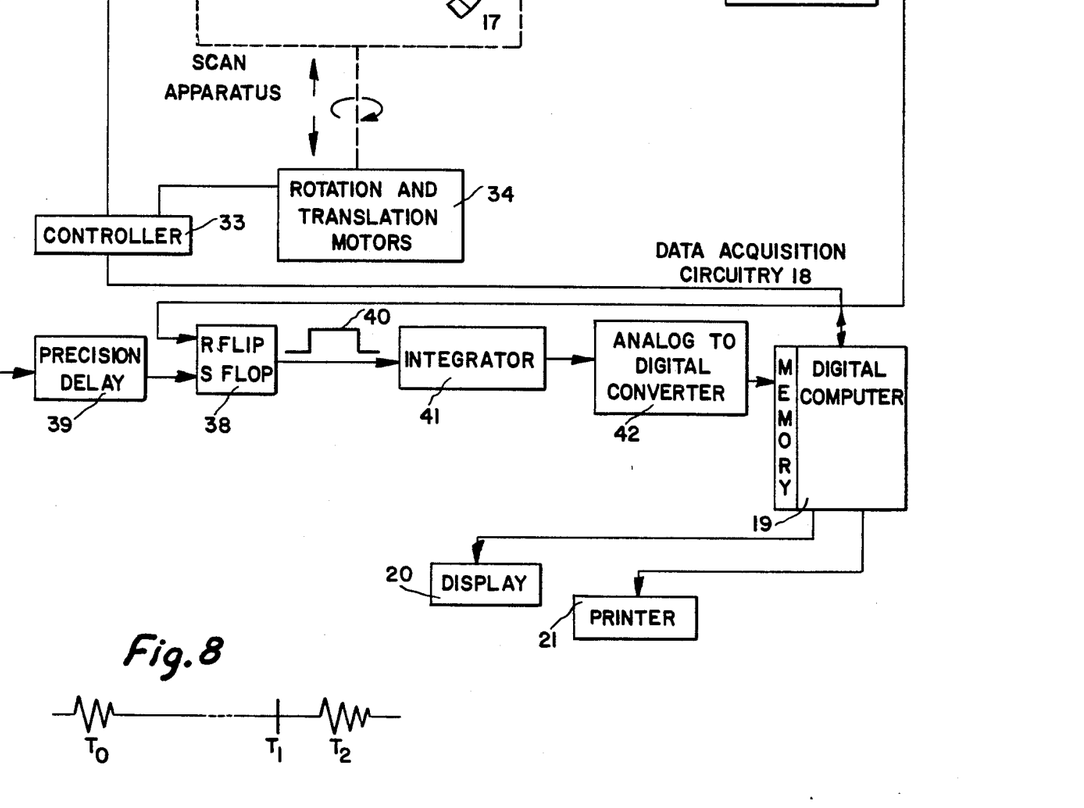
FIG. 7 is a computerized tomography system block diagram incorporating an exemplary embodiment of the data acquisition circuitry.
FIG. 8 is a timing diagram useful in explaining the operation of FIG. 7.

Details of one embodiment of the data acquisition circuitry and other features of the ultrasonic fan beam scanner are given in FIG. 7. The complete computerized tomography system is illustrated, and the scanner is used in a mode in which the scanner is controlled directly by the computer and the digital projection output data is fed into the computer memory unit. In the scan apparatus, liquid tank 11 (FIG. 2) is depicted schematically as a dashed line connecting the single transmitter 24 and arcuate receiver array 16. Under control of digital computer 19, a controller 33 energizes rotation and translation motors 34 to selectively move the scan apparatus in accordance with the operative sequence previously described. The rotation motor can be a 200 step stepping motor that is rotated through 1.8° per movement for 200 angular positions or through 3.6° per movement for 100 angular positions. The rotational scan may be either by discrete steps or in a continuous motion. After acquiring and processing data for the imaging of one specimen layer, the translation motor is energized to move the entire scan apparatus to a different axial position to acquire data for the imaging of a parallel specimen layer. At each angular position during the rotational scan, controller 33 signals a pulser circuit 35 to produce a start electrical pulse which in turn is fed to transmitter transducer 24 and initiates generation of an acoustic pulse. A compromise ultrasonic frequency for breast imaging, after considering a number of factors which affect the resolution and accuracy of the reconstruction, is typically 5 megahertz. The data acquisition circuitry has parallel processing channels for individual receiver transducers 17, only one of which is illustrated, the others being identical. Each processing channel includes a preamplifier 36 and a pulse height discriminator 37, such as comparator whose threshold is set just above the noise level. The leading edge of the acoustic pulse detected by the respective individual receiver defines the time of arrival, as was previously explained, and is determined by comparator 37. The propagation delay time stop signal generated by comparator 37 is fed to the reset input of a flip-flop circuit 38. The start electrical pulse generated by pulser 35 is delayed in a precision delay circuit 39 before being supplied to the set input of flip-flop 38. Consequently, the output of flip-flop 38 is a variable width pulse 40 indicative of the detected propagation delay time. To measure the delay time, an integrator circuit 41 converts variable width pulse 40 to an analog signal which is converted to digital form by an analog-to-digital converter 42 and read out to the memory unit of digital computer 19. The parallel processing channels respectively include a preamplifier, discriminator, flip-flop, integrator, and analog-to-digital converter, the outputs of all the channels being the digital projection output data.

The effect of using precision delay 39 to supply a delayed start pulse to the set input of flip-flop 38, rather than the start pulses itself, is explained with reference to FIG. 8. Assuming that the start pulse is generated by pulser 35 at time $T_o$, the interval $T_1-T_o$ representing the precision delay is the shortest possible time for the acoustic pulse to be detected by a receiver. If $T_2$ is the actual time of arrival of the acoustic pulse, the interval referenced to $T_1$ can be measured in the nanosecond range with good accuracy. Furthermore, the projection output data for all processing channels is available simultaneously at the computer for computation of reconstructions of velocity distributions. Using the ultrasonic fan beam scanner, velocity measurements can be obtained with a resolution of about 0.2 percent velocity difference relative to water. A rotational scan including data collection and read out is made in 10 seconds or less, thereby eliminating patient motion artifacts, so that reconstructions using this system are of excellent quality. As was previously explained, the computer results can be viewed on the visual display device 20 and/or printed out in numeric form using printer 21.

Figure 9:
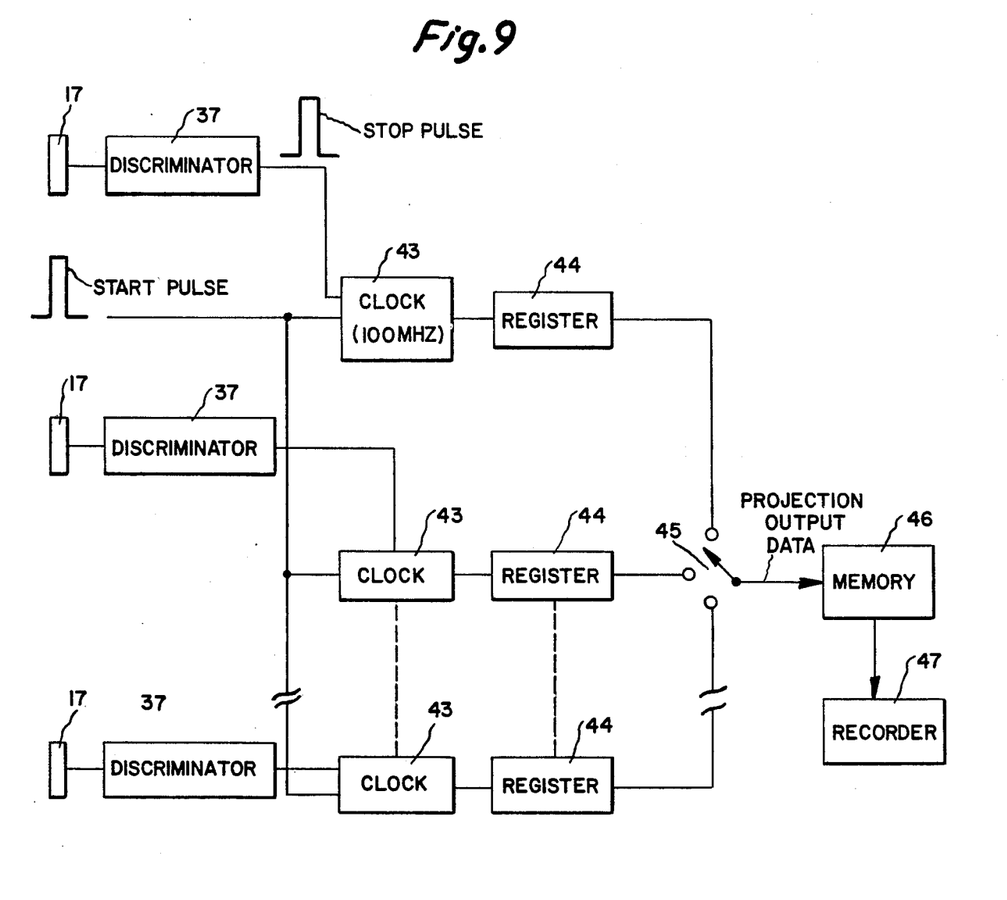
FIG. 9 is a block diagram of an alternative arrangement to that in FIG. 7 for measuring propagation delay times.

The essential features of a second embodiment of data acquisition circuitry for the ultrasonic fan beam scanner are shown diagrammatically in FIG. 9. Another mode of useage of the ultrasonic fan beam scanner is also described, in which the digital projection output data for one or more complete rotational scans is read into a memory unit and then into a recorder included in the scanner instrument. The ultrasonic scanner with memory and recorder consequently can be used in the doctor's office for mass screening for breast cancer, while a central computer later performs the computational analysis and generates images of velocity distributions or generates printouts as may be required. In the parallel processing channels, an individual receiver 17 is coupled to a preamplifier (not here shown) and pulse height discriminator 37 to thereby generate a propagation delay time stop pulse upon detection of a leading edge of an acoustic pulse. The processing channel further includes a clock or digital timing circuit 43 that is started by the start pulse produced by pulser 35 (FIG. 7), or by the delayed start pulse at the output of precision delay circuit 39, and stopped by the delay time stop pulse. Clock 43 operates at a 100 megahertz rate and accordingly derives extremely accurate measurements of time intervals indicative of the propagation delay time in that channel. The measured time interval is read out into a register 44 and is, of course, the digital projection output data. Before acquiring the next set of data at the next angular position of the scan apparatus, the contents of register 44 is read out serially by use of a switch 45 into a memory unit 46. The stored projection output data is next fed into a magnetic tape recording 47 or other type of recorder. Alternatively, of course, the projection output data can be transmitted directly to the computer for processing as previously explained.

Figure 10:
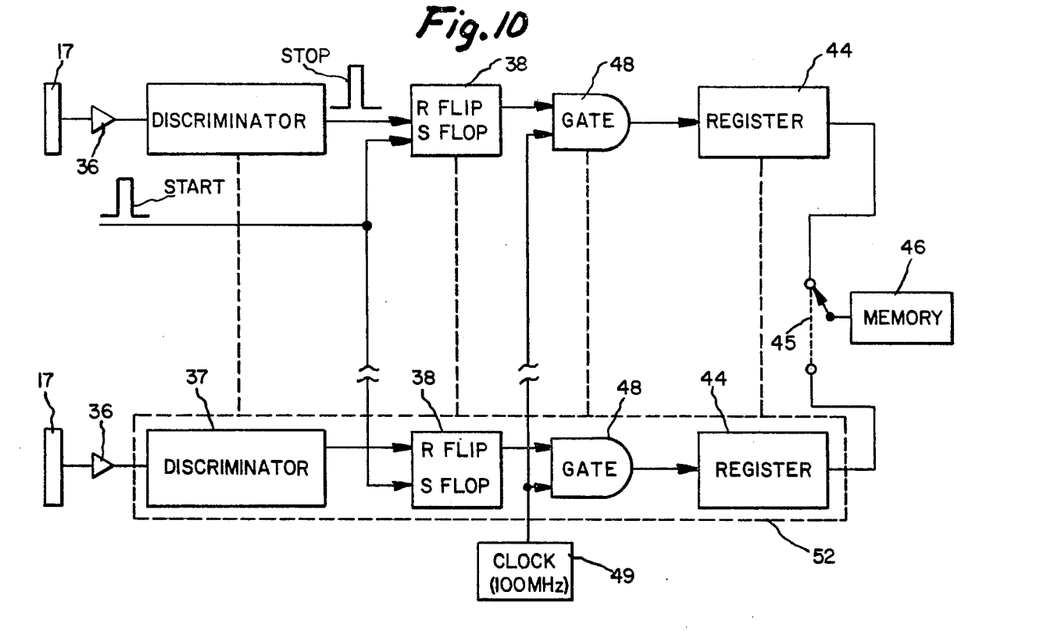
FIG. 10 is block diagram of a modification of the data acquisition circuit in FIG. 7 employing parallel channels and digital timing techniques.

FIG. 10 illustrates a modification and implementation of the data acquisition circuitry in FIG. 9 using simple logic circuits with an attendant reduction in drift and in the number of components as compared to the analog technique in FIG. 7. In this implementation, the digital timing circuit in the parallel processing channels, one per individual receiver, employs a common clock coupled through an enable gate to a high speed register. Thus, each channel has a flip-flop 38 which is set by the start pulse produced by pulser 35 (FIG. 7), or the delayed start pulse, and reset by the delay time stop pulse generated by pulse height discriminator 37 upon detection of an acoustic pulse by the respective receiver 17. An AND gate 48 has one input from a clock 49 producing pulses at a high rate such as 100 MHz, and is enabled by the output of flip-flop 38 to transmit the timing pulses to high speed register 44. The resulting count in the register is a measure of the time-of-flight. As before, digital data is acquired almost simultaneously and read out by means of switch 45 into memory 46.

Figure 11:
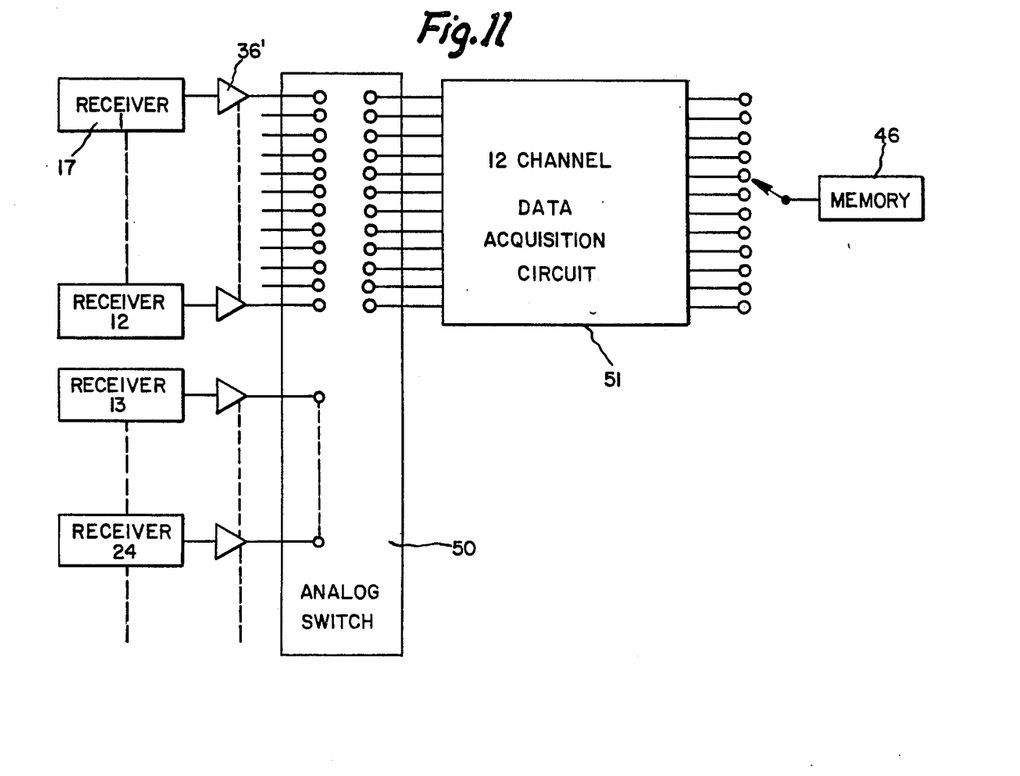
FIG. 11 shows another embodiment of the data acquisition circuit characterized by time sharing of the processing channels for systems with multiple pulsing of the transmitter.

Another embodiment of the data acquisition circuitry depicted in FIG. 11 uses time sharing of the electronics by the receiver channels to effect a savings in hardware. Although multiple transmitter pulsing is required at each angular position of the scan apparatus and the ultrasound dosage is thereby increased by some factor, there is no known tissue destruction at the power levels employed. Each channel has an amplifier 36' to bring the signal level from receiver transducer 17 up to a level where an analog switch 50 can operate satisfactorily. A small number of channels, such as 12, are simultaneousy selected and make connection to a 12 channel data acquisition circuit 51 having 12 parallel processing channels of digital circuitry of the type indicated at 62 in FIG. 10 with a common clock. Upon pulsing the transmitter transducer once to generate an acoustic pulse, the first set of receivers (1-12) are selected and projection output data is stored in the high speed registers and then read out serially into memory 46. Upon generating the next acoustic pulse at the same angular position, the next set of receivers (13-24) are selected and projection output data for that set is obtained and read out, and so on. The switching rate may be made very fast so that the data are acquired virtually simultaneously to make one projection. Corrections in the reconstruction algorithm can be made if the angular rate of rotation of the scan apparatus is too fast to allow this simultaneity approximation. In addition to the reduced component count, the number of comparators (discriminators 37) is small enough that they can be kept in alignment more readily than when using parallel channels with one comparator per receiver.

Figure 12A:
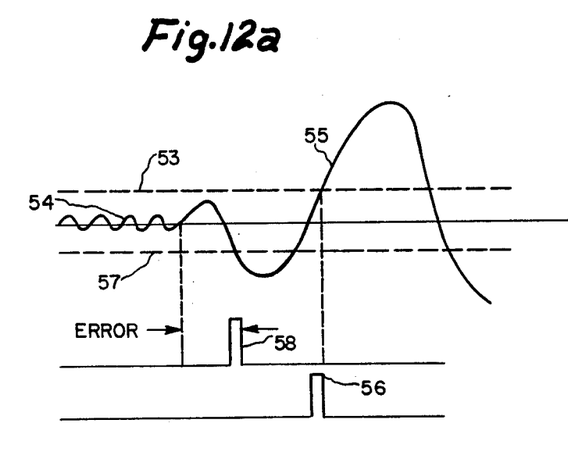
FIGS. 12a and 12b are respectively a waveform diagram and a block diagram relating to a bipolar comparator or discriminator arrangement for improved time-of-flight measurement.
Figure 12B:
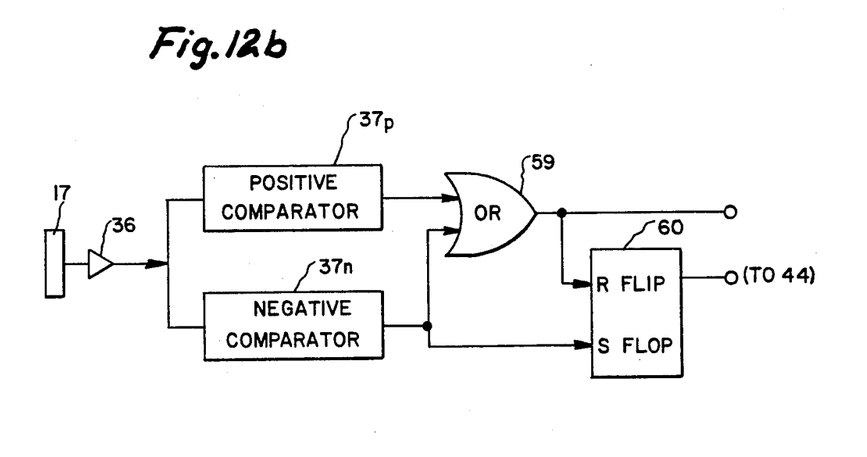

Improved accuracy and fidelity of the measured time-of-flight or propagation delay time is achieved by the bipolar comparator arrangement in FIG. 12b. The problem of accurate detection of received signals with an initial low level excursion below the comparator threshold voltage level is explained with reference to FIG. 12a. Assuming that a single comparator 37 with a positive threshold level 53 above the signal noise level 54 is included in the data acquisition circuit as previously explained, a low level initial excursion of the receiver signal 55 is missed and a positive comparator output pulse 56 is not generated until the second positive oscillation. The error is one rf cycle (200 nanoseconds at 5

MHz), too large to be ignored. Other acoustic pulses, on the other hand, have initial positive oscillations that rise about threshold 53 and are detected, giving rise to inherent errors in the time-of-flight measurements. By adding a paralleled negative comparator with a threshold voltage level 57, the first negative excursion of the signal greater than the threshold is detected and a negative output pulse 58 is generated at that time. The error is reduced but still has the magnitude indicated by the arrows, however, this can be compensated for by recognizing that the negative comparator has fired. The characteristics of the system are such that the received signal amplitude rises rapidly with the result that the first negative peak is usually above threshold even when the initial positive excursion is low level.

Accordingly, in FIG. 12b is a positive comparator 37p and negative comparators 37n, both used as pulse height discriminators, are fed the receiver signal from preamplifiers 36, and the outputs from the paralleled discriminators are in turn supplied to an OR logic circuit 59 to generate the delay time stop signal when the first comparator fires. The remainder of the data acquisition processing channel can be as in FIG. 10. To derive a polarity or correction indication, a flip-flop 60 is set by the output of negative comparator 37n and reset by the output of OR circuit 59, thereby producing a "1" bit that is supplied to register 44. When positive comparator 37p fires first, a "0" bit is generated by flip-flop 60. This correction bit is read out of register 44 along with the projection output data, and thus the computer can correct the data by subtracting a fixed time interval from the time-of-flight or delay time data for a correction bit indicating that the negative comparator has fired first. Since the variations in acoustic velocity values referenced to water are relatively small, the more accurate projection output data obtained with bipolar comparators enables the calculation of more precisely defined velocity distributions and, hence, improved images and numeric printouts.

While the use of a digital computer has been discussed, it will be appreciated by those skilled in the art that projection output data can be generated in analog form and processed in an analog-digital hybrid computer system. For further information particularly as to mechanical and general electrical features of a scanner instrument that can be adapted for usage as an ultrasonic fan beam scanner, assuming that the apparatus herein described is incorporated in such an instrument, reference may be made to copending application Ser. No. 723,941, filed on Sept. 16, 1976 by Robert Godbarsen et al, and entitled "X-Ray Body Scanner For Computerized Tomography". This application is assigned to the assignee of this invention and relates to an x-ray fan beam scanner for breast examination and imaging.

In summary, an ultrasonic scanner apparatus is described which measures a constitutively significant parameter of soft biological tissue. The techniques avoids many disadvantages of amplitude based ultrasonic systems, and in some ways is analogous to computerized transaxial x-ray tomography. The ability to accurately quantify two-dimensional velocity distributions, especially in view of the noninvasive nature of ultrasound and the rapid scan capability of the apparatus, suggests a unique application in mass screening for breast cancer detection.

While the invention has been particularly shown and described with reference to several preferred embodiments thereof, it will be understood by those skilled in the art that various changes in form and details may be made therein without departing from the spirit and scope of the invention.

The invention claimed is:

1. An ultrasonic scanner for computerized time-of-flight tomography comprising a scan apparatus having a rotational axis and including a generally sector-shaped tank having openings in opposing end walls, a transmitter transducer with an attached divergent lens mounted in one opening for producing a planar ultrasound fan beam, and an arcuate receiver transducer array mounted in the other opening and comprising multiple receiver transducers for individually detecting acoustic pulses propagating along divergent paths through a liquid bath and a tissue specimen immersed therein, means for rotating said scan apparatus, and means including a pulser circuit for generating start electrical pulses for periodically exciting said transmitter transducer and initiating generation of multiple acoustic pules approximately at each of a large number of equally spaced anagular positions of said scan apparatus, data acquisition circuit means operative approximately at each angular position for deriving digital projection output data indicative of acoustic pulse propagation delay times upon detection at individual receiver transducers, the ensemble of projection output data for the respective angular positions of the scan apparatus forming transmission time-of-flight projections to be used in combination to reconstruct velocity distributions at known coordinates in a specimen layer said data acquisition circuit means including a plurality of parallel processing channels, substantially smaller in number than the number of receiver transducers, that are switched in sequence among sets of said receiver transducers between generation of successive acoustic pulses at the respective angular positions, each channel comprising pulse height discriminator means for generating a delay time stop signal upon detection of acoustic pulses at a coupled receiver transducer, and further comprising a digital timing circuit including a digital clock that is effectively enabled by the respective start electrical pulse and stopped by the corresponding delay time stop signal to derive said projection output data, a register coupled to each timing circuit for temporarily receiving said projection output data, and a memory unit for storing said projection output data.

2. An ultrasonic scanner for computerized time-of-flight tomography comprising a scan apparatus having a rotational axis and including a tank that carries a transmitter transducer and also carries an arcuate receiver transducer array for individually detecting acoustic pulses propagating along divergent paths through a liquid path and specimen immersed therein, means for rotating said scan apparatus and for exciting said transmitter transducer to generate the acoustic pulses at selected angular positions of the scan apparatus, data acquisition means operative at each angular position for deriving projection output data indicative of acoustic pulse propagation delay times upon detection at individual receiver transducers, the ensemble of projection output data for the respective angular positions of the scan apparatus forming transmission time-of-flight projections to be used in combination to reconstruct velocity distributions at known coordinates in a specimen layer, said data acquisition means including multiple processing channels each comprising comparator pulse height discriminator means for generating a delay time stop signal upon the first excursion of a coupled receiver transducer signal to a magnitude exceeding either of predetermined positive and negative voltage levels, each channel further comprising means for utilizing the start electrical signal and delay time stop signal to derive said projection output data.

3. The ultrasonic scanner defined in claim 2 wherein the respective processing channels further include means for recognizing the polarity of the receiver signal upon generating said delay time stop signal and selectively adding a correction indication to said projection output data.

4. The ultrasonic scanner defined in claim 2 wherein said pulse height discriminator means comprises paralleled positive and negative comparators having their outputs connected to an OR logic current, said positive comparator producing said stop signal when the receiver signal first exceeds the predetermined positive voltage level and said negative comparator producing said stop signal when the receiver signal first exceeds the predetermined negative voltage level.

5. The ultrasonic scanner defined in claim 4 further including a flip-flop circuit which is set by the output of one of said comparators and reset by the output of said OR logic circuit to thereby selectively generate a correction bit for inclusion in said projection output data.

6. An ultrasonic scanner for computerized time-of-flight tomography comprising a scan apparatus having a rotational axis and including a tank on which is mounted a single transmitter transducer assembly for producing a planar ultrasound fan beam and on which is also mounted an arcuate receiver transducer array for individually detecting an acoustic pulse propagating along diverging paths of substantially equal path length through a liquid bath and tissue specimen immersed therein, means for rotating said scan apparatus and for exciting said transmitter transducer assembly to generate at least one acoustic pulse at each of a plurality of equally spaced angular positions of said scan apparatus, and data acquisition circuit means for deriving at each angular position digital projection output data indicative of the propagation delay times of the acoustic pulse upon detection at individual receiver transducers, the ensemble of projection output data for the respective angular positions of the scan apparatus forming transmission time-of-flight projections to be used in combination to reconstruct velocity distributions at known coordinates in a specimen layer, said means for exciting said transmitter transducer assembly including a pulser circuit operative to produce a start electrical pulse which initiates generation of the acoustic pulse, said data acquisition circuit means including parallel processing channels each comprising at lease one pulse height discriminator coupled to the respective receiver transducer for generating a delay time stop signal upon detection of the acoustic pulse, a flip-flop circuit that is effectively set by the start pulse and reset by said stop signal so as to produce as variable width pulse, an integrator circuit for converting the variable width pulse to an analog signal, and an analog-to-digital converter for converting the analog signal to said digital projection output data.

7. The ultrasonic scanner defined in claim 6 wherein said tank is at least partially sector-shaped with openings in opposing end walls in which are respectively mounted said transmitter transducer assembly and said arcuate receiver transducer array, said transmitter transducer assembly being comprised by a piezoelectric element with an attached divergent lens.

8. An ultrasonic scanner for computerized time-of-flight tomography comprising a scan apparatus having a rotational axis and including a tank on which is mounted a single transmitter transducer assembly for producing a planar ultrasound fan beam and on which is also mounted an arcuate receiver transducer array for individually detecting an acoustic pulse propagating along diverging paths through a liquid bath and tissue specimen immersed therein, means for rotating said scan apparatus and for exciting said transmitter transducer assembly to generate at least one acoustic pulse at each of a plurality of equally spaced angular positions of said scan apparatus, data acquisition circuit means for deriving at each angular position digital projection output data indicative of the propagation delay times of the acoustic pulse upon detection at individual receiver transducers, the ensemble of projection output data for the respective angular positions of the scan apparatus forming transmission time-of-flight projections to be used in combination to reconstruct velocity distributions at known coordinates in a specimen layer, means for translating said scan apparatus incrementally in the direction of the rotational axis, whereby projection output data can be derived at multiple axial positions to be used to reconstruct velocity distributions for multiple parallel specimen layers, and a memory unit for storing said projection output data, said transmitter transducer assembly being comprised by a piezoelectric element with an attached divergent lens, and said means for exciting said transmitter transducer assembly including a pulser circuit operative to product a start electrical pulse which initiates generation of the acoustic pulse and is also supplied to trigger a delay circuit, said data acquisition circuit means including parallel processing channels each comprising a pulse height discriminator coupled to the respective receiver transducer for generating a delay time stop signal upon detection of the acoustic pulse, a flip-flop circuit that is set by the delay circuit output and reset by said stop signal so as to produce a variable with pulse, an integrator circuit for converting the variable width pulse to an analog signal, and an analog-to-digital converter for converting the analog signal to said digital projection output data.

9. An ultrasonic scaner for computerized time-of-flight tomography comprising
a scan apparatus having a rotational axis and including a tank on which is mounted a single transmitter transducer assembly for producing a planar ultrasound fan beam and on which is also mounted an arcuate receiver transducer array for individually detecting an acoustic pulse propagating along diverging paths of substantially equal path length through a liquid bath and tissue specimen immersed therein,
means for rotating said scan apparatus and for exciting and transmitter transducer assembly to generate at least one acoustic pulse at each of a plurality of equally spaced angular positions of scan apparatus, and
data acquisition circuit means for deriving at each angular position digital projection output data indicative of the propagation delay times of the acoustic pulse upon detection at individual receiver transducers, the ensemble of projection output data for the respective angular positions of the scan apparatus forming transmission time-of-flight projections to be used in combination to reconstruct velocity distributions at known coordinates in a specimen layer,
said means for exciting said transmitter transducer assembly including a pulser circuit operative to produce a start electrical pulse which initiates generation of the acoustic pulse,
said data acquisition circuit means including parallel processing channels each comprising at least one pulse height discriminator coupled to the respective receiver transducer for generating a delay time stop signal upon detection of the acoustic pulse, each channel further comprising a digital timing circuit including a digital clock that is effectively enabled for the measurement of time by the start pulse and stopped by the stop signal to thereby generate said digital projection output data.

10. The ultrasonic scanner defined in claim 9 wherein said tank has openings in opposing end walls in which are respectively mounted said transmitter transducer assembly and said arcuate receiver transducer array, said transmitter transducer assembly including a piezoelectric element with an attached divergent lens.

11. The ultrasonic scanner defined in claim 10 further including a memory unit for storing said projection output data, and means for translating said scan apparatus incrementally in the direction of the rotational axis, whereby projection output data can be derived at a plurality of axial positions to be used to reconstruct velocity distributions for a plurality of parallel specimen layers.

* * * * *

UNITED STATES PATENT OFFICE
CERTIFICATE OF CORRECTION

Patent No. 4,075,883  Dated February 28, 1978

Inventor(s) Gary H. Glover

It is certified that error appears in the above-identified patent and that said Letters Patent are hereby corrected as shown below:

Col. 3, line 68, "pulses" should read -- pulse --

Col. 4, line 40, "transmitted" should read -- transmitter --;
line 47, "slide" should read -- slice --.

Col. 5, line 25, the formula should read:

$$t_\theta = \int_\mathcal{L} \frac{ds}{v} \; ;$$

line 31, "the" second occurrence should read -- and --.

Col. 6, line 10, "summar" should read -- summary --

Col. 9, line 16, cancel "is".

Col. 10, line 23, "pules" should read -- pulses --;
line 35, after "layer" insert a comma

UNITED STATES PATENT OFFICE
CERTIFICATE OF CORRECTION

Patent No. 4,075,883   Dated February 28, 1978

Inventor(s) Gary H. Glover

It is certified that error appears in the above-identified patent and that said Letters Patent are hereby corrected as shown below:

Col. 12, line 6, "as" should read - a -
        line 55, "product" should read - produce -
        line 65, "with" should read - width -.

Col. 13, line 13, "and" should read - said -.

Signed and Sealed this

*Fifteenth* Day of *August 1978*

[SEAL]

Attest:

RUTH C. MASON
*Attesting Officer*

DONALD W. BANNER
*Commissioner of Patents and Trademarks*